United States Patent [19]

Connell et al.

[11] Patent Number: 5,747,505
[45] Date of Patent: May 5, 1998

[54] HETEROCYCLIC ARYL-, ALKYL- AND CYCLOALKYLACETAMIDES

[75] Inventors: Richard Connell, Trumbull, Conn.; Siegfried Goldmann, Wuppertal, Germany; Ulrich Müller, Wuppertal, Germany; Martin Beuck, Erkrath, Germany; Hilmar Bischoff, Wuppertal, Germany; Dirk Denzer, Wuppertal, Germany; Rudi Grützmann, Solingen, Germany; Stefan Wohlfeil, Hilden, Germany

[73] Assignee: Bayer Aktiengesellschaft, Leverkusen, Germany

[21] Appl. No.: 717,027

[22] Filed: Sep. 20, 1996

[30] Foreign Application Priority Data

Sep. 29, 1995 [DE] Germany ............... 19536378.7

[51] Int. Cl.$^6$ ............... C07D 215/12; C07D 217/12; C07D 409/12; A61K 31/47

[52] U.S. Cl. ............... 514/307; 514/311; 514/314; 514/336; 514/340; 514/342; 514/344; 514/345; 514/351; 514/438; 514/441; 514/444; 514/445; 514/461; 514/471; 514/473; 546/146; 546/148; 546/152; 546/175; 546/176; 546/250; 546/256; 546/261; 546/265

[58] Field of Search ............... 514/210, 222.2, 514/228.8, 241, 247, 307, 299, 311, 336, 345, 438, 461; 546/250, 152, 146; 544/1, 53, 67, 88, 98, 242, 336; 548/121, 122, 123, 124, 125, 400, 469, 950; 549/59, 52, 295, 323

[56] References Cited

U.S. PATENT DOCUMENTS

| | | | |
|---|---|---|---|
| 4,248,788 | 2/1981 | Bourgery et al. | 260/340.3 |
| 4,970,215 | 11/1990 | Mohrs et al. | 514/311 |
| 5,310,744 | 5/1994 | Raddatz et al. | 514/314 |
| 5,352,687 | 10/1994 | Müller et al. | 514/341 |
| 5,420,149 | 5/1995 | Müller et al. | 514/399 |
| 5,521,206 | 5/1996 | Müller et al. | 514/400 |
| 5,527,809 | 6/1996 | Müller-Gliemann et al. | 514/303 |

FOREIGN PATENT DOCUMENTS

| | | |
|---|---|---|
| 0 545 170 A1 | 6/1993 | European Pat. Off. . |
| 42 00 954 A1 | 10/1992 | Germany . |
| 380129 | 9/1964 | Switzerland . |

OTHER PUBLICATIONS

R. Stauffer: Synthèse de nouvelles tryptamines substituées, Helvetica Chimica Acta, Bd. 49, Nr. 3, 1966, 1199–1203.

J.C. Gaignault et al: Indolylméthyl–1 tétrahydro–1,2,3, 4–isoquinoléines et benzyl–1 tétrahydro2,3,4,9/1H/beta–c-arbolines formées à partir de la tryptamine et de ses dérivés, Annales Pharmaceutiques Francaises, Bd. 36, Nr. 9–10, 1978, 401–408.

Bodanszky, The Practice of Peptide Synthesis: Springer Verlag, vol. 21, 1984, 1984, pp. VIII–XVII.

Organic Chemistry; Functional Group Transformations: Academic Press, vol. 12–1 (1983).

J. Org. Chem., 1968, 33, 2902.

Primary Examiner—Johann Richter
Assistant Examiner—Jane C. Osweckí
Attorney, Agent, or Firm—Sprung Kramer Schaefer & Briscoe

[57] ABSTRACT

The heterocyclic aryl-, alkyl- and cycloalklacetamides are prepared by reacting the appropriately substituted acetic acids with amines, if appropriate in complexed form. The heterocyclic aryl-, alkyl- and cycloalkylacetamides can be used as active compounds in medicaments, in particular in antiatherosclerotic medicaments.

8 Claims, No Drawings

HETEROCYCLIC ARYL-, ALKYL- AND CYCLOALKYLACETAMIDES

The present invention relates to heterocyclic aryl-, alkyl- and cycloalkyl-acetamides, a process for their preparation and their use as medicaments, in particular as antiatherosclerotic medicaments.

It is known that raised blood levels of triglycerides (hypotriglyceridaemia) and cholesterol (hypocholesterolaemia) are associated with the genesis of atherosclerotic vascular wall changes and coronary heart diseases.

A distinctly increased risk of the development of coronary heart disorders moreover exists if these two risk factors occur in combination, in turn accompanied by an overproduction of apolipoprotein B-100. There is therefore still a great need to make available active medicaments for the control of atherosclerosis and coronary heart diseases.

The present invention relates to heterocyclic aryl-, alkyl- and cycloalkyl-acetamide derivatives of the general formula (I)

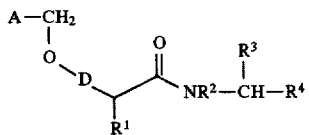

in which
- A represents aryl having 6 to 10 carbon atoms, or represents a 5- to 7-membered aromatic, optionally benzofused heterocycle having up to 3 heteroatoms from the series S, N and/or O, where the rings are optionally substituted identically or differently up to 3 times by halogen, nitro, cyano, trifluoromethyl, hydroxyl, carboxyl or straight-chain or branched alkyl, alkoxy, acyl or alkoxycarbonyl each having up to 8 carbon atoms,
- D represents naphthyl, cycloalkyl having 3 to 6 carbon atoms or a 4- to 6-membered, saturated or unsaturated, optionally benzo-fused heterocycle having up to 3 heteroatoms from the series S, N and/or O, where the cycles are optionally substituted identically or differently up to 2 times by halogen, cyano, hydroxyl or straight-chain or branched alkyl or alkoxy each having up to 4 carbon atoms,
- $R^1$ represents hydrogen, cycloalkyl having 3 to 10 carbon atoms or straight-chain or branched alkyl having 1 to 10 carbon atoms, or represents phenyl which is optionally substituted identically or differently up to 2 times by halogen, cyano, hydroxyl, straight-chain or branched alkyl or alkoxy each having up to 4 carbon atoms,
- $R^2$ represents hydrogen or straight-chain or branched alkyl having up to 3 carbon atoms,
- $R^3$ represents hydrogen or straight-chain or branched alkyl having up to 5 carbon atoms or benzyl, or represents cycloalkyl having 3 to 7 carbon atoms, or represents phenyl or a 5- to 7-membered aromatic heterocycle having up to 3 heteroatoms from the series S, N and/or O, each of which is optionally substituted identically or differently up to 3 times by halogen, nitro, phenyl, hydroxyl or straight-chain or branched alkyl or alkoxy each having up to 6 carbon atoms, and
- $R^4$ represents hydrogen or a group of the formula —$CH_2$—OH or $CH_2$—O—CO—$R^5$, in which
- $R^5$ denotes hydrogen, straight-chain or branched alkyl having up to 8 carbon atoms or phenyl which is optionally substituted identically or differently up to 3 times by halogen, hydroxyl, cyano or straight-chain or branched alkyl or alkoxy each having up to 4 carbon atoms, and their salts.

The heterocyclic aryl-, alkyl and cycloalkylacetamides according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention, which have a free carboxyl group. Those particularly preferred are, for example, sodium, potassium, magnesium or calcium salts, and also ammonium salts which are derived from ammonia, or organic amines, for example ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a known manner.

Heterocycle, optionally benzo-fused, in the context of the invention in general represents a saturated or unsaturated 4- to 7-membered, preferably 5- to 6-membered, heterocyclic which can -contain up to 3 heteroatoms from the series S, N and/or O and which, in the case of a nitrogen atom, can also be bonded via this. Examples which may be mentioned are: indolyl, quinolyl, benzo[b]thienyl, benzo[b]furyl, pyridyl, thienyl, furyl, pyrrolyl, thiazolyl, oxazolyl, imidazolyl, morpholinyl or piperidyl. Quinolyl, furyl, pyridyl and thienyl are preferred.

Preferred compounds of the general formula (I) are those in which
- A represents phenyl, quinolyl, indolyl, isoquinolyl, benzo[b]furyl, benzo[b]thienyl or pyridyl, each of which is optionally substituted identically or differently up to 2 times by fluorine, chlorine, bromine, nitro, cyano, trifluoromethyl, hydroxyl, carboxyl or straight-chain or branched alkyl, alkoxy, acyl or alkoxycarbonyl each having up to 6 carbon atoms,
- D represents naphthyl, cyclobutyl, cylcopentyl, cyclohexyl, pyridyl, furyl, thienyl, piperidinyl, pyrimidinyl, piperazinyl, pyridazinyl or azetidinyl, each of which is optionally substituted by fluorine, chlorine, bromine, cyano, hydroxyl, methyl or methoxy,
- $R^1$ represents hydrogen, cyclobutyl, cyclopentyl, cyclohexyl, cycloheptyl, cyclooctyl or straight-chain or branched alkyl having up to 7 carbon atoms, or represents phenyl which is optionally substituted by fluorine, chlorine, bromine, cyano, hydroxyl or straight-chain or branched alkyl or alkoxy each having up to 3 carbon atoms, $R^2$ represents hydrogen or methyl, $R^3$ represents hydrogen or straight-chain or branched alkyl having up to 4 carbon atoms, benzyl, cyclopropyl, cyclopentyl, cyclohexyl or phenyl, pyridyl, thienyl or furyl, each of which is optionally substituted identically or differently up to 2 times by fluorine, chlorine, bromine, phenyl, nitro, hydroxyl or straight-chain or branched alkyl or alkoxy having up to 4 carbon atoms, and $R^4$ represents hydrogen or a group of the formula $-CH_2-OH$ or $-CH_2-O-CO-R^5$, in which $R^5$ denotes hydrogen, straight-chain or branched alkyl having up to 6 carbon atoms or phenyl, which is optionally substituted identically or differently up to 2 times by fluorine, chlorine, bromine, cyano, hydroxyl or straight-chain or branched alkyl or alkoxy each having up to 3 carbon atoms, and their salts.

Particularly preferred compounds of the general formula (I) are those in which

A represents phenyl, quinolyl, or pyridyl, each of which is optionally substituted by fluorine, chlorine, bromine, cyano or straight-chain or branched alkyl, alkoxy, acyl or alkoxycarbonyl each having up to 3 carbon atoms, D represents naphthyl, cyclobutyl, cyclopentyl, cyclohexyl, furyl, pyridyl, thienyl, azetidinyl or piperidinyl, each of which is optionally substituted by fluorine, cyano, hydroxyl, methyl or methoxy, $R^1$ represents hydrogen, cyclohexyl, cycloheptyl, cyclooctyl or straight-chain or branched alkyl having up to 6 carbon atoms, or represents phenyl which is optionally substituted by fluorine, chlorine, cyano, hydroxyl, methyl or methoxy, $R^2$ represents hydrogen or methyl, $R^3$ represents hydrogen or straight-chain or branched alkyl having up to 3 carbon atoms, benzyl, cyclopropyl, cyclopentyl, cyclohexyl or pyridyl, thienyl or phenyl, each of which is optionally substituted identically or differently up to 2 times by fluorine, chlorine, bromine, nitro, phenyl, hydroxyl or straight-chain or branched alkyl or alkoxy having up to 3 carbon atoms, and $R^4$ represents hydrogen, a group of the formula $-CH_2-OH$ or $-CH_2-O-CO-R^5$, in which $R^5$ denotes straight-chain or branched alkyl having up to 6 carbon atoms or phenyl, which is optionally substituted identically or differently up to 2 times by fluorine, chlorine, bromine, cyano, hydroxyl, methyl or methoxy, and their salts.

A process for the preparation of the compounds of the general formula (I) according to the invention has additionally been found, characterized in that carboxylic acids or esters of the general formula (II)

in which

A, D and $R^1$ have the meaning given above, and $R^6$ represents hydrogen or straight-chain or branched alkyl having up to 4 carbon atoms, are reacted with amines of the general formula (III)

in which $R^2$, $R^3$ and $R^4$ have the meaning given above, if appropriate in complexed form in inert solvents and in the presence of bases and/or auxiliaries.

The process according to the invention can be illustrated by way of example by the following reaction scheme:

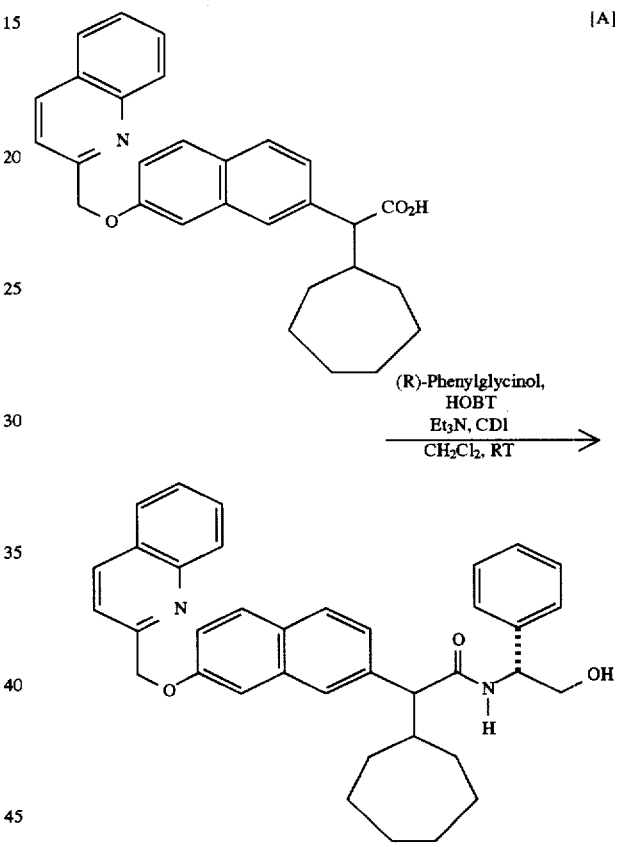

Suitable solvents in this context are inert organic solvents which do not change under the reaction conditions. These include ethers, such as diethyl ether or tetrahydrofuran, halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Dichloromethane, tetrahydrofuran, toluene and dimethylformamide are particularly preferred.

Bases which can be employed for the process according to the invention are in general inorganic or organic bases. These preferably include alkali metal hydroxides, for example sodium hydroxide or potassium hydroxide, alkaline earth metal hydroxides, for example barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium and their hydrides such as sodium hydride. Sodium and potassium carbonate and triethylamine are preferred.

The base is employed in an amount from 1 mol to 5 mol, preferably from 1 mol to 3 mol, relative to 1 mol of the compound of the general formula (II).

Suitable auxiliaries also are dehydrating agents. These include, for example, carbodiimides such as diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or iso-butyl chloroformate or benzotriazolyloxy-tris-(dimethylamino)phosphonium hexafluorophosphate or diphenyl phosphoramidate or methane-sulphonyl chloride, if appropriate in the presence of bases such as triethylamine or N-ethylmorpholine or N-methylpiperidine or dicyclohexylcarbodiimide and N-hydroxysuccinimide.

The reaction is in general carried out in a temperature range from 0° C. to 150° C., preferably from +20° C. to +110° C.

The reaction can be carried out at normal, elevated or reduced pressure (e.g. 0.5 to 5 bar). In general, it is carried out at normal pressure.

Suitable complexed amines are metal complexes, the metal complex-forming component in general being $C_1$–$C_4$-aluminium or tin alkyls, for example $(CH_3)_3Al$ or $Sn[N(Si(CH_3)_3)_2]_2$. $(CH_3)_3Al$ is preferred.

The compounds of the general formula (II) are known or can be prepared, for example, by

[A] reacting compounds of the general formula (IV)

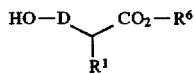 (IV)

in which

D, $R^1$ and $R^6$ have the meaning given above, with compounds of the general formula (V)

A—$CH_2$—L (V)

in which

A has the meaning given above and

L represents sulphonates, for example mesylate or tosylate, or represents halogen, preferably chlorine or bromine, in inert solvents and in the presence of bases and/or auxiliaries, or

[B] reacting compounds of the general formula (VI)

A—$CH_2$—OH (VI)

in which

A has the meaning given above, with compounds of the general formula (VII)

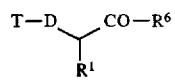 (VII)

in which

D, $R^1$ and $R^6$ have the meaning given above and

T represents triflate or halogen, preferably iodine or bromine, in inert solvents, if appropriate in the presence of bases and/ or auxiliaries, or

[C] converting compounds of the general formula (VIII)

A—$CH_2$—O—D'—H (VIII)

in which

A has the meaning given above, and

D' represents the optionally substituted radical of the formula

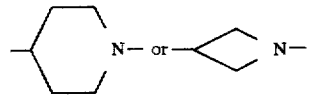

first by reaction with aldehydes of the formula (IX)

$R^1$—CHO (IX)

in which $R^1$ has the meaning given above, and diethyl cyanophosphate in inert solvents into the compounds of the general formula (X)

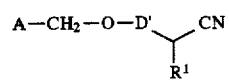 (X)

in which

A, D' and $R^1$ have the meaning given above, in a second step converting with alcohols in the presence of acids into the corresponding esters, and in the case of the acids hydrolysing the esters.

Customary organic solvents suitable for the processes are those which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide, tetrahydrofuran and dimethyl sulphoxide are preferred.

Suitable alcohols for the processes are in general those such as methanol, ethanol, propanol, isopropanol, butanol, iso-butanol or tert-butanol, tert-Butanol is preferred.

Bases which can be employed for the processes are in general inorganic or organic bases. These preferably include alkali metal hydroxides, for example sodium hydroxide or potassium hydroxide, alkaline earth metal hydroxides, for example barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or alkyllithium compounds, for example methyl-, sec-butyl or tert-butyllithium, or organic amines (trialkyl($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium or their hydrides such as sodium hydride. Those preferred are sodium hydride, potassium carbonate, triethylamine, pyridine and potassium tert-butoxide, DBU or DABCO.

In general, the base is employed in an amount from 0.05 to 10 mol, preferably from 1 mol to 2 mol, relative to 1 mol of the compound of the formulae (V) and (VII).

Suitable auxiliaries for the reaction of the compounds of the general formula (VII) are in general copper(I) bromide, $CuCO_3$, $Cu(OH)_2$, Cu(I)I, Cu, CuO, CuCl, Cu bronze, $Cu_2O$ or silver oxides. Copper bromide is preferred.

The auxiliary is in general employed in an amount from 0.01 mol to 100 mol, preferably from 0.1 mol to 10 mol, relative to 1 mol of the compound of the general formula (VII).

The processes according to the invention are in general carried out in a temperature range from –30° C. to +100° C., preferably from –10° C. to +60° C.

The processes according to the invention are in general carried out at normal pressure. However, it is also possible to carry out the processes at elevated pressure or at reduced pressure (e.g. in a range from 0.5 to 5 bar).

Suitable auxiliaries are the dehydrating reagents mentioned above.

The preparation of the various amine/amide derivatives can also be carried out using a multiplicity of known methods, for example the coupling of acid derivatives from peptide chemistry [cf. for this purpose Bodanszky, The Practice of Peptide Synthesis: Springer Verlag, Vol. 21, 1984 and Organic Chemistry; Functional Group Transformations: Academic Press, Vol. 12-1].

The acid-binding agents and dehydrating reagents are in general employed in an amount from 0.5 to 3 mol, preferably from 1 to 1.5 mol, relative to 1 mol of the compounds of the general formulae (IV) and (VII).

The hydrolysis of the carboxylic acid esters is carried out according to customary methods, by treating the esters with customary bases in inert solvents.

Suitable bases for the hydrolysis are the customary inorganic bases. These preferably include alkali metal hydroxides or alkaline earth metal hydroxides, for example sodium hydroxide, potassium hydroxide or barium hydroxide, or alkali metal carbonates such as sodium or potassium carbonate or sodium hydrogen carbonate. Those particularly preferably employed are sodium hydroxide or potassium hydroxide.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide.

Those particularly preferably used are alcohols such as methanol, ethanol, propanol, or isopropanol. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (e.g. from 0.5 to 5 bar).

When carrying out the hydrolysis the base is in general employed in an amount from 1 to 3 mol, preferably from 1 to 1.5 mol, relative to 1 mol of the ester. Molar amounts of the reactants are particularly preferably used.

Suitable acids for the hydrolysis are in general protonic acids, for example sulphuric acid, HCl or HBr. Sulphuric acid is preferred.

The acid is employed in an amount from 0.01 mol to 200 mol, preferably from 0.1 mol to 20 mol, in each case relative to 1 mol of the compounds of the general formula (VIII).

The compounds of the general formulae (IV), (V), (VI), (VII), (VIII), (IX) and (X) are known in some cases or are new and in these cases can be prepared according to customary methods.

The compounds of the general formula (III) are known per se.

The compounds of the general formula (I) according to the invention have an unforeseeable spectrum of pharmacological action.

They can be used as active compounds in medicaments for the reduction of changes to vascular walls and for the treatment of coronary heart disorders, cardiac insufficiency, disorders of brain function, ischaemic brain disorders, apoplexy, circulatory disorders, microcirculation disorders and thromboses.

Furthermore, the proliferation of smooth muscle cells plays a decisive part in the occlusion of vessels. The compounds according to the invention are suitable for inhibiting this proliferation and thus for preventing atherosclerotic processes.

The compounds according to the invention are distinguished by a lowering of ApoB-100-associated lipoproteins (VLDL and its degradation products, e.g. LDL), of ApoB-100, of triglycerides and of cholesterol. They thus have useful pharmacological properties which are superior in comparison with the prior art.

Surprisingly, the action of the compounds according to the invention first consists in a reduction or complete inhibition of the formation and/or the release of ApoB-100-associated lipoproteins from liver cells, which results in a lowering of the VLDL plasma level. This lowering of VLDL must be accompanied by a lowering of the plasma levels of ApoB-100, LDL, triglycerides and cholesterol; several of the abovementioned risk factors which are involved in vascular wall changes are thus simultaneously reduced.

The compounds according to the invention can therefore be employed for the prevention and treatment of atherosclerosis, obesity, pancreatitis and constipation.

1. Inhibition of the release of ApoB-100-associated lipoproteins

The test for detecting the inhibition of the release of ApoB-100-associated lipoproteins-from liver cells was carried out in vitro using cultivated liver cells, preferably using cells of the human line HepG2. These cells are grown under standard conditions in medium for the culture of eukaryotic cells, preferably in RPMI 1640 with 10% foetal calf serum. HepG2 cells synthesize and secrete into the culture supernatant ApoB-100-associated lipoprotein particles which in principle are constructed similarly to the VLDL and LDL particles which are to be found in the plasma.

These particles can be detected using an immunoassay for human LDL. This immunoassay is carried out using antibodies which have been induced against human LDL in the rabbit under standard conditions. The anti-LDL antibodies (rabbit anti-LDL Ab) were purified by affinity chromatography on an immunosorbent using human LDL. These purified rabbit anti-LDL Ab are adsorbed on the surface of plastic. Expediently, this adsorption takes place on the plastic surface of microtiter plates having 96 wells, preferably on MaxiSorp plates. If ApoB-100-associated particles are present in the supernatant of Hep-G2 cells, these can bind to the insolubilized rabbit anti-LDL Ab and an immune complex is formed which is bound to the plastic surface. Non-bound proteins are removed by washing. The immune complex on the plastic surface is detected using monoclonal antibodies which have been induced against human LDL and purified according to standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific light absorption at 450 nm is determined, which is a measure of the amount of ApoB-100-associated particles which have been secreted into the culture supernatant by the HepG2 cells.

Surprisingly, the compounds according to the invention inhibit the release of the ApoB-100-associated particles. The $IC_{50}$ value indicates at which substance concentration the light absorption is inhibited by 50% in comparison with the control (solvent control without substance).

| Ex. No. | $IC_{50}$ [$10^{-9}$ mol/l] |
| --- | --- |
| 1 | 195 |
| 2 | >2000 |
| 3 | 71 |
| 4 | 11 |
| 5 | 622 |
| 6 | 255 |
| 7 | 1792 |
| 8 | 1883 |
| 9 | >2000 |
| 10 | >2000 |
| 11 | >2000 |
| 12 | >2000 |
| 13 | 235 |
| 14 | 235 |

2. Determination of VLDL secretion in vivo in the hamster

The effect of the test substances on VLDL secretion in vivo is investigated in the hamster. To do this, golden hamsters are anaesthetized with Ketavet (83 mg/kg s.c.) and Nembutal (50 mgkgi.p.) after premedication with atropine (83 mg/kg s.c.). When the animals have become reflex-free, the jugular vein is exposed and cannulated. 0.25 ml/kg of a 20% strength solution of Triton WR-1339 in physiological saline solution is then administered. This detergent inhibits lipoprotein lipase and thus leads to a rise in the triglyceride level as a result of a lack of metabolism of secreted VLDL particles. This triglyceride rise can be used as a measure of the VLDL secretion rate. Blood is taken from the animals before and one and two hours after administration of the detergent by puncture of the retroorbital venous plexus. The blood is incubated for two hours at room temperature, then overnight at 4° C. in order to finish clotting completely. It is then centrifuged at 10,000 g for 5 minutes. The triglyceride concentration in the serum thus obtained is determined with the aid of a modified commercially available enzyme test (Merckotest® triglyceride No. 14354). 100 µl of serum are mixed with 100 µl of test reagent in 96-hole plates and incubated at room temperature for 10 minutes. The optical density is then determined at a wavelength of 492 nm in an automatic plate-reading apparatus (SLT spectra). Serum samples having too high a triglyceride concentration are diluted with physiological saline solution. The triglyceride concentration contained in the samples is determined with the aid of a standard curve measured in parallel. In this model, test substances are either administered intravenously immediately before administration of the detergent or orally or subcutaneously before initiation of anaesthesia.

3. Inhibition of intestinal triglyceride absorption in vivo (rats)

The substances which are to be investigated for their triglyceride absorption-inhibiting action in vivo are administered orally to male Wistar rats having a body weight of between 170 and 230 g. For this purpose, the animals are divided into groups of 6 animals 18 hours before substance administration and the feed is then withdrawn from them. Drinking water is available to the animals ad libitum. The animals of the control groups receive an aqueous tragacanth suspension or a tragacanth suspension which contains olive oil. The tragacanth-olive oil suspension is prepared using an Ultra-Turrax. The substances to be investigated are suspended in an appropriate tragacanth-olive oil suspension, likewise using an Ultra-Turrax, directly before substance administration.

Blood is taken from each rat by a puncture of the retroorbital venous plexus before stomach tube application to determine the basal serum triglyceride content. The tragacanth suspension, the tragacanth-olive oil suspension without substance (control animals), or the substance suspended in an appropriate tragacanth-olive oil suspension are then administered to the fasting animals using a stomach tube. Further taking of blood to determine the post-prandial serum triglyceride rise is carried out as a rule 1, 2 and 3 hours after stomach tube application.

The blood samples are centrifuged and, after recovering the serum, the triglycerides are determined photometrically using an EPOS analyzer 5060 (Eppendorf Geratebau, Netherler & Hinz GmbH, Hamburg). The determination of the triglycerides is carried out completely enzymatically using a commercially available UV test.

The post-prandial serum triglyceride rise is determined by subtraction of the triglyceride preliminary value of each animal from its corresponding post-prandial triglyceride concentrations (1, 2 and 3 hours after administration).

The differences (in mmol/l) at each time (1, 2 and 3 hours) are averaged in the groups and the average values of the serum triglyceride rise ($\Delta TG$) of the substance-treated animals are compared with the animals which only received the tragacanth-oil suspension.

The serum triglyceride course of the control animals which only received tragacanth is also calculated. The substance effect at each time (1, 2 or 3 hours) is determined as follows and indicated in $\Delta\%$ of the oil-loaded control.

$$\Delta\%\ \text{Triglyceride rise} = \frac{\Delta TG_{Substance} - \Delta TG_{Tragacanth\ control}}{\Delta TG_{Oil\ loading} - \Delta TG_{Tragacanth\ control}} \times 100$$

Effect of 10 mg of test substance/kg of body weight p.o. on the triglyceride rise ($\Delta\%$) 2 h after a triglyceride loading in the serum of fasting rats. The serum triglyceride rise of fat-loaded control animals relative to the serum triglyceride level of tragacanth control animals corresponds to 100%. n=6 animals per group.

The statistical assessment is carried out using student's t test after prior checking of the variances for homogeneity.

Substances which statistically significantly ($p<0.05$) decrease by at least 30% the post-prandial serum triglyceride rise at one point, compared with the untreated control group, are regarded as pharmacologically active.

4. Inhibition of VLDL secretion in vivo (rats)

The action of the test substances on VLDL secretion is also investigated in the rat. To do this, Triton WR-1339 (2.5 mg/kg), dissolved in physiological saline solution, is administered intravenously into the tail vein of rats of body weight 500 g Triton WR-1339 inhibits lipoprotein lipase and thus leads through inhibition of VLDL catabolism to a rise in the triglyceride and cholesterol level. These rises can be used as a measure of the VLDL secretion rate.

Blood is taken from the animals before and 1 and 2 hours after administration of the detergent by puncture of the retroorbital venous plexus. The blood is incubated at room temperature for 1 h for clotting and the serum is recovered by centrifugation at 10 000 g for 20 s. The triglycerides are then determined photometrically at a wavelength of 540 nm by means of a commercially available coupled enzyme test (Sigma Diagnostics®, No. 339). Measurement is carried out with the aid of a likewise coupled enzyme test (Boehringer Mannheim®, No. 1442350) at a wavelength of 546 nm. Samples having triglyceride or cholesterol concentrations which exceed the measuring range are diluted with physiological saline solution. The determination of the respective serum concentrations is carried out with the aid of standard series measured in parallel. Test substances are administered orally, intravenously or subcutaneously immediately after the Triton injection.

The invention additionally relates to the combination of heterocyclic aryl-, alkyl- and cycloalkylacetamides of the general formula (I) with a glycosidase and/or amylase inhibitor for the treatment of familial hyperlipidaemias, of obesity (adiposity) and of diabetes mellitus. Glucosidase and/or amylase inhibitors in the context of the invention are, for example, acarbose, adiposine, voglibase, miglitol, emiglitate, MDL-25637, camiglibase (MDL-73945), tendamistat, AI-3688, trestatin, pradimilin-Q and salbostatin.

The preferred combination is that of acarbose, miglitol, emiglitate or voglibase with one of the abovementioned compounds of the general formula (I) according to the invention.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this context, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, where, for example, if water is used as a diluent organic solvents can optionally be used as auxiliary solvents.

Administration is carried out in the customary manner, preferably orally or parenterally, in particular perlingually or intravenously.

In the case of parenteral administration, solutions of the active compound can be employed using suitable liquid excipient materials.

In general, it has proven advantageous in the case of intravenous administration to administer amounts of approximately 0.001 to 1 mg/kg, preferably approximately 0.01 to 0.5 mg/kg, of body weight to achieve effective results, and in the case of oral administration the dosage is approximately 0.01 to 20 mg/kg, preferably 0.1 to 10 mg/kg, of body weight.

In spite of this, it may, if appropriate, be necessary to deviate from the amounts mentioned, namely depending on the body weight or the type of administration route, on individual behaviour towards the medicament, the manner of its formulation and the time or interval at which administration takes place. Thus in some cases it may be sufficient to manage with less than the abovementioned minimum amount, while in other cases the upper limit mentioned has to be exceeded. In the case of the administration of relatively large amounts, it may be advisable to divide these into several individual doses over the course of the day.

| Abbreviations used: | |
|---|---|
| bs = | broad singlet |
| CI = | chemical ionization |
| cHept = | cyclo-heptyl |
| cHex = | cyclo-hexyl |
| cPent = | cyclo-pentyl |
| CDI = | N'-(3-dimethylaminopropyl)-N'-ethylcarbodiimide |
| d = | doublet |
| dia = | diastereomer |
| dd = | doublet of doublets |
| DMF = | N,N-dimethylformamide |
| DMSO = | dimethyl sulphoxide |
| EI = | electron impact ionization |
| FAB = | fast atom bombardment |
| HOBT = | 1-hydroxy-1H-benzotriazole |
| Hz = | Hertz |
| iBu = | isobutyl |
| iPr = | isopropyl |
| m = | multiplet |
| Me = | methyl |
| Ph = | phenyl |
| RT = | room temperature |
| s = | singlet |
| t = | triplet |
| TFA = | trifluoroacetic acid |
| THF = | tetrahydrofuran |
| TMS = | tetramethylsilane |

| Solvent mixtures used | | |
|---|---|---|
| Petroleum ether:acetone = | 1:1 | (A) |
| Petroleum ether:ethyl acetate = | 10:1 | (B) |
| Petroleum ether:ethyl acetate = | 5:1 | (C) |
| Petroleum ether:ethyl acetate = | 2:1 | (D) |
| Petroleum ether:ethyl acetate = | 1:1 | (E) |
| Petroleum ether:ethyl acetate = | 2:1 | (F) |
| Dichloromethane | | (G) |
| Dichloromethane:methanol = | 50:1 | (H) |
| Dichloromethane:methanol = | 20:1 | (I) |
| Dichloromethane:methanol = | 10:1 | (J) |
| Dichloromethane:ethyl acetate = | 1:1 | (K) |
| Dichloromethane:ethanol = | 50:1 | (L) |
| Petroleum ether:ethyl acetate = | 20:1 | (M) |
| Petroleum ether:ethyl acetate = | 3:1 | (N) |
| Toluene:ethyl acetate = | 1:1 | (O) |
| Ethyl acetate:methanol = | 10:1 | (P) |

Starting compounds

EXAMPLE I

Ethyl 2-cycloheptyl-2-(7-methoxy-3,4-dihydro-naphth-2-yl)acetate

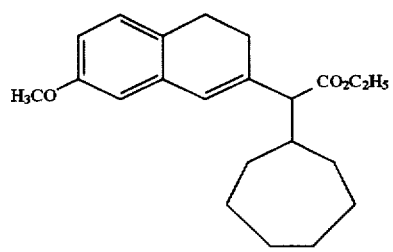

Sodium hydride (0.59 g, 14.7 mmol, 60% strength in paraffin) is initially introduced into anhydrous DMF (1.5 ml)

under argon. The mixture is cooled to 0° C. Ethyl 2-(7-methoxy-3,4-dihydro-naphthalen-2-yl)acetate (3.3 g, 13.4 mmol) and cycloheptyl bromide (2.61 g, 14.7 mmol) are dissolved in DMF (5 ml) and added dropwise. The mixture is stirred at 0° C. for 1 hour, and overnight while gradually warming to room temperature. It is poured onto water and CH$_2$Cl$_2$, and the separated aqueous phase is extracted a further three times with CH$_2$Cl$_2$. The combined organic phases are dried using sodium sulphate and evaporated. The residue is purified by column chromatography:

Yield: 2.60 g (57%)

R$_f$=0.67 (CH$_2$Cl$_2$);

mass (calculated) for C$_{22}$H$_{30}$O$_3$=342.48; mass spectrum (CI(NH$_3$), rel. intensity) 360 (M+NH$_4^+$, 100%), 343 (18%);

$^1$H NMR (250 MHz, CDCl$_3$/TMS) δ7.00 (d, J=8.08 Hz, 1H), 6.65 (dd, J=8.11 Hz, J=2.68 Hz, 1H), 6.60 (d, J=2.59 Hz, 1H), 6.34 (s, 1H), 4.15 (m, 2H), 3.77 (s, 3H), 2.95 (d, J=10.9 Hz, 1H), 2.71 (m, 2H), 2.37 (m, 1H), 2.28 (m, 1H), 2.10 (m, 1H), 1.72–1.14 (m, 12H), 1.23 (t, J=7.08 Hz, 3H).

EXAMPLE II

Ethyl 2-cycloheptyl-2-(7-methoxy-naphth-2-yl)acetate

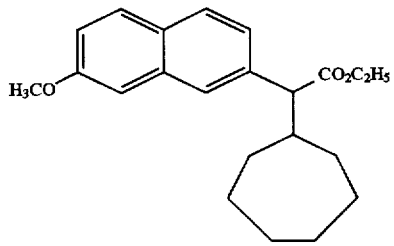

2.60 g (7.6 mmol) of the compound from Example I and tetrachloro-p-benzoquinone (2.80 g, 11.4 mmol) are dissolved in xylene (20 ml) and heated at reflux for 8 hours. The mixture is cooled and the xylene is evaporated in a rotary evaporator. CH$_2$Cl$_2$ is added to the residue and the crystals which are deposited are filtered off with suction and dried. The mother liquor is concentrated in a rotary evaporator and purified by column chromatography together with the crystals:

Yield: 1.56 g (60%)

R$_f$=0.40 (Petroleum ether:ethyl acetate 10:1);

mass (calculated) for C$_{22}$H$_{28}$O$_3$=340.47; mass spectrum (CI(NH$_3$), rel. intensity) 360 (M+NH$_4^+$, 100%);

$^1$H NMR (250 MHz, CDCl$_3$/TMS) δ7.75–7.62 (m, 3H), 7.35 (dd, J=8.47 Hz, J=1.95 Hz, 1H), 7.15–7.05 (m, 2H), 4.20–3.99 (m, 2H), 3.91 (s, 3H), 3.42 (d, J=10.98 Hz, 1H), 2.35 (m, 1H), 1.90–1.10 (m, 11H), 1.20 (t, J=7.12 Hz, 3H), 1.05 (m, 1H).

EXAMPLE III

Ethyl 2-cycloheptyl-2-(7-hydroxy-naphth-2-yl)acetate

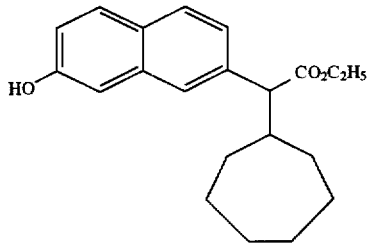

0.5g (1.47 mmol) of the compound from Example II is dissolved in CH$_2$Cl$_2$ (10 ml). The solution is cooled to −78° C. and treated with boron tribromide (1M solution in CH$_2$Cl$_2$, 7.34 ml, 7.34 mmol). The solution is warmed to −30° C. and, after an hour, to 0° C. After an hour, the solution is again cooled to −30° C. and treated with ethanol (10 ml). It is allowed to stir overnight at room temperature. It is concentrated in a rotary evaporator and the residue is diluted with water and ethyl acetate. The phases are separated and the organic phase is dried over sodium sulphate and concentrated in a rotary evaporator. The residue is purified by column chromatography:

Yield: 0.358 g (75%)

M.p.: 106° C.

R$_f$=0.43 (3:1; Petroleum ether:ethyl acetate);

mass (calculated) for C$_{21}$H$_{26}$O$_3$=326.44; mass spectrum (CI(NH$_3$), rel. intensity) 344 (M+NH$_4^+$, 100%);

$^1$H NMR (300 MHz, CDCl$_3$/TMS) δ7.70 (d, J=8.68 Hz, 2H), 7.59 (bs, 1H), 7.35 (dd, J=8.50 Hz, J=1.68 Hz, 1H), 7.10 (d, J=1.46 Hz, 1H) 7.05 (dd, J=8.73 Hz, J=2.51 Hz, 1H), 4.10 (m, 2H), 3.41 (d, J=10.96 Hz, 1H), 2.37 (m, 1H), 1.70–1.20 (m, 11H), 1.19 (t, J=7.20 Hz, 3H), 1.00 (m, 1H).

EXAMPLE IV 1,1-Dimethoxy-2-iodo-1-(6-methoxynaphth-2-yl)ethane

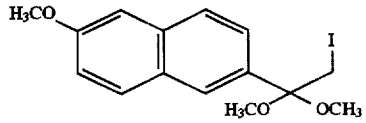

2-Acetyl-6-methoxynaphthalene (18.8 g, 93.9 mmol) is initially introduced into trimethyl orthoformate (76.0 g, 93.4 mmol) in a dark flask. Iodine (28.6 g, 112.7 mmol) is added thereto. The mixture is stirred overnight at room temperature. Saturated aqueous Na$_2$S$_2$O$_3$ solution is then added and this solution is extracted with CH$_2$Cl$_2$ (3×). The combined organic phases are combined and dried over Na$_2$SO$_4$ and concentrated in a rotary evaporator. The residue is flash-chromatographed:

Yield: 19.5 g (56%)

M.p.: 95°–96° C.

R$_f$=0.33 (20:1; petroleum ether:ethyl acetate);

$^1$H NMR (200 MHz, CDCl$_3$/TMS) δ7.94 (m, 1H), 7.76–7.71 (m, 2H), 7.46 (dd, J=1.82 Hz, 1H), 7.17–7.14 (m, 2H), 3.92 (s, 3H), 3.59 (s, 2H), 3.25 (s, 6H).

EXAMPLE V

Methyl 2-(6-Methoxynaphth-2-yl)acetate

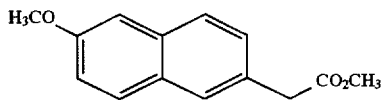

4.1 g (11.01 mmol) of the compound from Example IV are dissolved in trimethyl orthoformate (11.0 g, 103 mmol). Methanol (11.0 ml) and, with exclusion of light, $AgBF_4$ (2.14 g, 11.01 mmol) are added thereto. The mixture is stirred overnight at room temperature. Water and $CH_2Cl_2$ are then added to it and the insoluble silver salts are filtered off with suction. The mixture is then extracted. The combined organic phases are dried over $Na_2SO_4$ and concentrated in a rotary evaporator. The residue is flash-chromatographed:

Yield: 1.8 g (71%)

M.p. 70° C.;

$R_f$=0.14 (20:1; petroleum ether:ethyl acetate);

mass (calculated) for $C_{14}H_{14}O_3$=230.27; mass spectrum (FAB, rel. intensity) 230 (70%), 171 (100%);

$^1$H NMR (300 MHz, CDCl$_3$) δ7.71–7.65 (m, 3H), 7.36 (dd, J=8.44 Hz, J=1.81 Hz, 1H), 7.15–7.11 (m, 2H), 3.91 (s, 3H), 3.75 (s, 2H), 3.70 (s, 3H).

EXAMPLE VI

Methyl 2-cyclopentyl-2-(6-methoxynaphth-2-yl)acetate

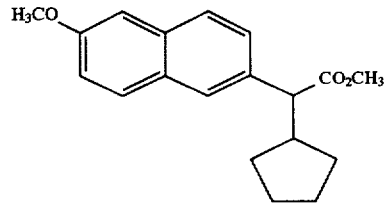

Potassium tertiary-butoxide (4.52 g, 40.2 mmol) is dissolved in DMF (10.0 ml). The solution is then cooled to 0° C. 6.45 g (28.0 mmol) of the compound from Example V are dissolved in DMF (30.0 ml) and added dropwise, the mixture is stirred at 0° C. for 30 minutes and a solution of cyclopentyl bromide (6.53 g, 43.7 mmol) in DMF (5.0 ml) is added dropwise. The temperature climbs gradually to room temperature and the mixture is stirred overnight. $H_2O$ is added and the resulting precipitate is filtered off with suction and dried. The crystals are recrystallized using methanol:

Yield: 5.43 g (65%)

M.p. 115° C;

$R_f$=0.25 (20:1; petroleum ether:ethyl acetate);

mass (calculated) for $C_{19}H_{22}O_3$=298.38; mass spectrum (EI, rel. intensity) 298 (65%), 229 (100%), 171 (100%);

$^1$H NMR (200 MHz, CDCl$_3$/TMS) δ7.78–7.67 (m, 3H), 7.45 (dd, J=8.55 Hz, J=1.58 Hz, 1H), 7.16–7.11 (m, 2H), 3.91 (s, 3H), 3.65 (s, 3H), 3.41 (d, J=11.13 Hz, 1H), 2.65 (m, 1H), 1.95 (m, 1H), 1.75–1.20 (m, 6H), 1.05 (m, 1H).

EXAMPLE VII

Methyl 2-cyclopentyl-2-(6-hydroxynaphth-2-yl)acetate

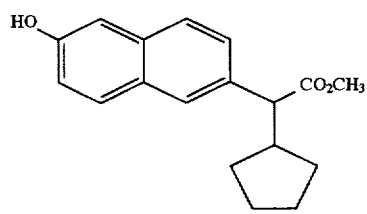

The reaction is carried out with 6.83 g (23 mmol) of the compound from Example VI, 1N BBr$_3$ in CH$_2$Cl$_2$ (100 ml, 100 mmol) analogously to the procedure for Example III:

Yield: 5.87 g (90%)

$R_f$=0.40 (50:1; CH$_2$Cl$_2$:methanol);

mass (calculated) for $C_{18}H_{20}O_3$=284.36; mass spectrum (EI, rel. intensity) 284 (35%), 43 (100%);

$^1$H NMR (200 MHz, CDCl$_3$/TMS) δ7.80–7.60 (m, 3H), 7.42 (dd, J=8.53 Hz, J=1.77 Hz, 1H), 7.20–7.05 (m, 2H), 3.65 (s, 3H), 3.39 (d, J=11.1 Hz, 1H), 2.70 (m, 1H), 1.95 (m, 1H), 1.70–1.20 (m, 6H), 1.03 (m, 1H).

EXAMPLE VIII 2-(5-Benzyloxy-2-pyridin-2-yl)-2-cycloheptylacetonitrile

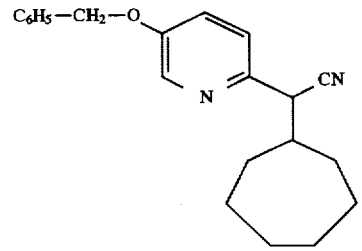

Sodium hydride (183 mg, 4.58 mmol, 60% strength in paraffin) is initially introduced into anhydrous DMF (5 ml) under argon. A solution of 5-benzyloxy-2-cyanomethylpyridine (1.0 g, 4.16 mmol) in DMF (3 ml) is added dropwise to this at 0° C. The mixture is allowed to come to room temperature and, after 30 minutes, is again cooled to 0° C. A solution of cycloheptyl bromide (0.81 g, 4.58 mmol) in DMF (3 ml) is added dropwise. The mixture is stirred at room temperature for 2 hours. The solution is treated with water and extracted 3 times using ether. The combined organic phases are dried over sodium sulphate and concentrated in a rotary evaporator. The residue is purified by column chromatography:

Yield: 0.83 g (62%)

$R_f$=0.53 (3:1; petroleum ether:ethyl acetate);

mass (calculated) for $C_{21}H_{24}N_2O$=320.44; mass spectrum (CI (NH$_3$), rel. intensity) 321 (M+H, 100%), 224 (60%), 91 (70%);

$^1$H NMR (250 MHz, TMS/CDCl$_3$) δ8.34 (m, 1H), 7.48–7.5 (m, 7H), 5.11 (s, 2H), 3.87 (d, J=5.82 Hz 1H), 2.20 (m, 1H), 1.70–1.40 (m, 12H).

EXAMPLE IX 2-(5-Benzyloxy-2-pyridin-2-yl)-2-cyclopentylacetonitrile

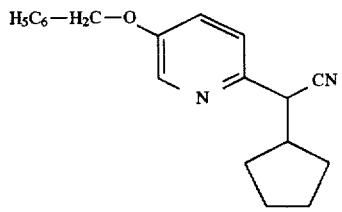

The reaction is carried out analogously to the procedure for Example VIII using 1.0 g (4.16 mmol) of 5-benzyloxy-2-cyanomethylpyridine, sodium hydride (0.18 g, 4.58 mmol) and cyclopentyl bromide (0.68 g, 4.58 mmol):

Yield: 693 mg (57%)

$R_f$=0.61 (3:1; petroleum ether:ethyl acetate);

mass (calculated) for $C_{19}H_{20}N_2O$=292.38; mass spectrum (CI (NH$_3$), rel. intensity) 293 (M+H, 30%), 224 (30%), 91 (100%);

$^1$H NMR (250 MHz, CDCl$_3$/TMS) δ8.32 (m, 1H), 7.45–7.32 (m, 5H), 7.31–7.22 (m, 2H), 5.10 (s, 2H), 3.90 (d, J=6.44 Hz, 1H), 2.48 (m, 1H), 1.88–1.40 (m, 8H).

EXAMPLE X

Methyl 2-(5-Hydroxy-2-pyridin-2-yl)-2-cycloheptylacetate

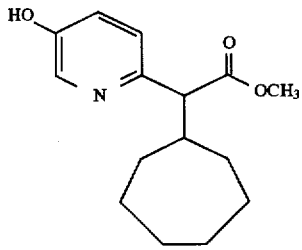

2.0 g (6.24 mmol) of the compound from Example VIII are dissolved hot in methanol (8 ml). Concentrated sulphuric acid (3 ml) is added to this solution and everything is boiled under reflux together for 5 hours. The mixture is cooled and diluted with ethyl acetate (50 ml) and cautiously neutralized with saturated sodium hydrogen carbonate solution. The organic phase is dried over sodium sulphate and evaporated. The residue is purified by column chromatography:

Yield: 0.79 g (52%)

M.p. 141° C.;

$R_f$=0.54 (1:1; petroleum ether:ethyl acetate);

mass (calculated) for $C_{15}H_{21}NO_3$=263.34; mass spectrum (CI (NH$_3$), rel. intensity) 264 (M+H, 100%), 167 (60%), 135 (40%);

$^1$H NMR (200 MHz, CDCl$_3$/TMS) δ8.09 (d, J=2.61 Hz, 1H), 7.40–7.23 (m, 2H), 3.62 (s, 3H), 3.63 (d, J=10.71 Hz, 1H), 2.35 (m, 1H), 1.80–1.15 (m, 11H), 1.05 (m, 1H).

EXAMPLE XI

Methyl 2-(5-Hydroxy-2-pyridin-2-yl)-2-cyclopentylacetate

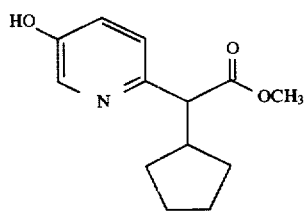

The reaction is carried out analogously to the procedure of Example X using 0.732 g (2.5 mmol) of the compound from Example IX, methanol (5 ml) and conc. sulphuric acid (1.1 ml).

Yield: 0.290 g (49%)

M.p. 112° C.;

$R_f$(1:1; petroleum ether:ethyl acetate)=0.45;

mass (calculated) for $C_{13}H_{17}NO_3$=235.29; mass spectrum (FAB, rel. intensity) 236 (100%), 176 (60%);

$^1$H NMR (200 MHz, CDCl$_3$/TMS) δ8.09 (dd, J=2.78 Hz, J=0.58 Hz, 1H), 7.34 (dd, J=8.60 Hz, J=0.45 Hz, 1H) 7.23 (dd, J=8.59 Hz, J=2.88 Hz, 1H), 3.63 (s, 3H), 3.56 (d, J=11.10 Hz, 1H), 2.60 (m, 1H), 1.90 (m, 1H), 1.70–1.20 (m, 6H), 1.03 (m, 1H).

EXAMPLE XII

Ethyl 2-cycloheptyl-2-(thiophen-2-yl)acetate

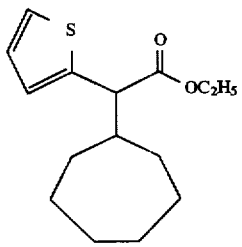

Ethyl thienylacetate (17.0 g; 100 mmol) is initially introduced into anhydrous TMF (170 ml) and the mixture is cooled to 0° C. Sodium hydride (6.0 g, 150 mmol) is added to this in portions. The mixture is stirred for 30 minutes and cycloheptyl bromide (53 g, 300 mmol) is then added dropwise. The mixture is stirred overnight while gradually warming to room temperature. DMF is removed in a rotary evaporator under a high vacuum and the residue is then extracted in ethyl acetate and saturated NH$_4$Cl solution. The organic phase is washed a further 2 times with water, dried over sodium sulphate and concentrated in a rotary evaporator. The residue is purified by column chromatography:

Yield: 21 g (79%)

$R_f$=0.80 (10:1; petroleum ether:ethyl acetate);

mass (calculated) for $C_{15}H_{22}O_2S$=266.40; mass spectrum (CI (NH$_3$), rel. intensity) 267 (20%), 170 (100%), 97 (30%);

$^1$H NMR (250 MHz, CDCl$_3$/TMS) δ7.18 (m, 1H), 6.95–6.90 (m, 2H), 4.11 (m, 2H), 3.62 (d, J=10.15 Hz 1H), 2.15 (m, 1H), 1.85–1.20 (m, 11H), 1.27 (t, J=7.1 Hz, 3H), 1.15 (m, 1H).

EXAMPLE XIII

Ethyl 2-cycloheptyl-2-(5-bromothiophen-2-yl) acetate

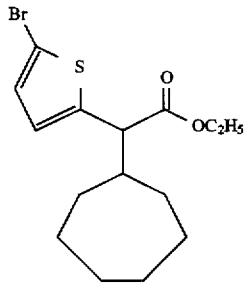

9.37 g (35.2 mmol) of the compound from Example XII are reacted with N-bromosuccinimide (6.89 g, 38.7 mmol) at room temperature in a 1:1 mixture of chloroform and acetic acid (42 ml) [reference: J. Org. chem., 1968, 33, 2902]. After 2 hours, the starting material has disappeared; the mixture is extracted with $CH_2Cl_2$ and aqueous sodium hydrogen carbonate solution and the organic phase is dried with sodium sulphate and evaporated in vacuo.

Yield: 12 g (99%)

$R_f$=0.73 (toluene)

EXAMPLE XIV

N-(tert-Butoxycarbonyl)-4-hydroxypiperidine

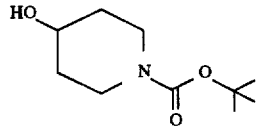

4-Hydroxypiperidine (83.7 g, 827.9 mmol) is dissolved in 800 ml of methanol and cooled to 0° C. A solution of di-tert-butyl dicarbonate (198.8 g 910.7 mmol) in 400 ml of methanol is added dropwise. The mixture is stirred overnight at room temperature. The solution is concentrated in a rotary evaporator and the residue is purified by means of a flash column.

Yield: 157 g (94%)

$R_f$=0.36 (1:1; ethyl acetate:cyclohexane);

Mass (calculated) for $C_{10}H_{19}NO_3$=201.27; mass spectrum (FAB, rel. intensity) 201 (5%), 145 (25%), 128 (25%), 57 (100%);

$^1$H NMR (200 MHz, CDCl$_3$) δ3.88–3.80 (m, 3H, CH$_2$ CH(OH)CH$_2$ and NCH$_2$CH$_2$), 3.08–2.95 (m, 2H, N CH$_2$CH$_2$), 1.89–1.81 (m, 2H, CH(OH)CH$_2$CH$_2$), 1.54–1.36 (m, 2H, CH(OH)CH$_2$CH$_2$, 1.45 (s, 9H, NCO$_2$C(CH$_3$)$_3$).

EXAMPLE XV 4-(Quinolin-2-ylmethoxy)piperidine

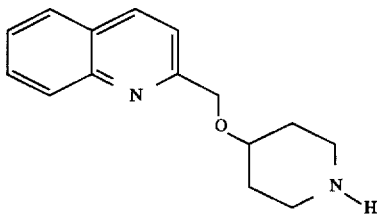

27.5 g (80.3 mmol) of N-(tert-butoxycarbonyl)-4-(quinolin-2-ylmethoxy)piperidine (Example XXIII) are dissolved in CH$_2$Cl$_2$ (250 ml). Trifluoroacetic acid (91.6 g, 803 mmol) is added to this solution. The mixture is heated at reflux overnight. It is cooled and covered with a layer of water (1000 ml) and extracted. The aqueous phase is extracted again with CH$_2$Cl$_2$ and then cooled. It is rendered alkaline using 2N sodium hydroxide solution. It is then extracted 2× using CH$_2$Cl$_2$. The combined organic phases are dried over Na$_2$SO$_4$ and concentrated in a rotary evaporator:

Yield: 14.0 g (72%)

$R_f$=0.10 (CH$_2$Cl$_2$; methanol 10:1);

mass (calculated) for $C_{15}H_{18}NO_2$=242.32; mass spectrum (EI, rel. intensity) 242 (10%), 158 (50%), 143 (100%), 85 (60%);

$^1$H NMR (300 MHz, CDCl$_3$) δ8.17 (d, J=8.50 Hz 1H), 8.05 (d, J=8.50 Hz, 1H), 7.18 (dd, J=8.09 Hz, J=0.7 Hz, 1H), 7.60 (m, 2H), 7.50 (m, 1H), 4.85 (s, 2H, OCH$_2$-quinoline), 3.56 (m, 1H, quinoline-CH$_2$O CH(CH$_2$—)$_2$), 3.15–3.07 (m, 2H, NCH$_2$CH$_2$), 2.66–2.56 (m, 2H, NCH$_2$CH$_2$), 2.06–1.98 (m, 2H, CH(OR)CH$_2$), 1.63–1.48 (m, 2H).

EXAMPLE XVI

2-Phenyl-[4-(quinolin-2-ylmethoxy)-piperidin-1-yl]-acetonitrile

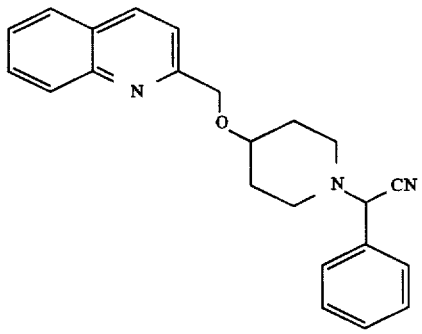

9.8 g (40 mmol) of the compound from Example XV are suspended in THF (200 ml). This suspension is added to a mixture of benzaldehyde (5.0 g, 50 mmol) and diethyl cyanophosphate (7.8 g, 48 mmol) in THF (100 ml). The mixture is stirred overnight at room temperature. The THF is stripped off in a rotary evaporator and the residue is purified by flash chromatography:

Yield: 13.2 g (91%);

$R_f$=0.18 (3:1, ethyl acetate:petroleum ether);

mass (calculated) for $C_{23}H_{23}N_3O=357.46$; mass spectrum (CI (NH$_3$), rel. intensity) 358 (70%), 331 (100%);

$^1$H NMR (200 MHz, CDCl$_3$/TMS) δ8.17 (d, J=8.50 Hz, 1H), 8.04 (d, J=8.45 Hz, 1H), 7.81 (bd, J=8.13 Hz, 1H), 7.70 (m, 1H), 7.65 (d, J=8.50 Hz, 1H), 7.59–7.32 (m, 6H), 4.86 (s, 1H, NC$\underline{H}$(Ph)CN), 4.83 (s, 2H, OC$\underline{H}_2$-quinoline), 3.57 (m, 1H, quinoline-CH$_2$OC$\underline{H}$(CH$_2$—)$_2$), 2.87 (m, 1H), 2.73 (m, 1H), 2.51 (m, 1H), 2.30 (m, 1H), 2.02–1.91 (m, 2H), 1.91–1.58 (m, 2H).

EXAMPLE XVII

Ethyl 2-cycloheptyl-2-(7-(quinolin-2-ylmethoxy)-naphth-2-yl)acetate

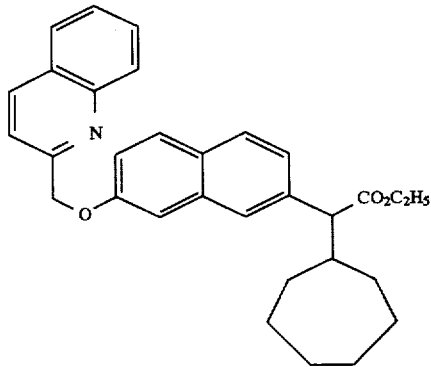

Sodium hydride (0.132 g, 3.31 mmol, 60% strength in paraffin) is initially introduced into anhydrous DMF (1 ml) under argon. 0.9 g (2.76 mmol) of the compound from Example III, dissolved in DMF (5 ml), is added dropwise at 0° C. to this mixture. It is allowed to come to room temperature and, after 30 minutes, is again cooled to 0° C. 0.54 g (3.03 mmol) of 2-chloromethylquinoline in DMF (4 ml) is added dropwise. The mixture is stirred overnight at room temperature. The solution is treated with water and extracted 3 times with ether. The combined organic phases are dried over sodium sulphate and concentrated in a rotary evaporator. The residue is purified by column chromatography:

Yield: 1.21 g (94%);

R$_f$=0.73 (3:1, petroleum ether:ethyl acetate);

R$_f$=0.79 (50:1, CH$_2$Cl$_2$:methanol);

mass (calculated) for $C_{31}H_{23}NO_3=467.61$; mass spectrum (CI (NH$_3$), rel. intensity) 468 (80%), 144 (100%);

$^1$H NMR (200 MHz, CDCl$_3$/TMS) δ8.22–8.02 (m, 2H), 7.88–7.66 (m, 5H), 7.64–7.51 (m, 2H), 7.36 (dd, J=8.48 Hz, J=1.70 Hz, 1H), 7.31–7.19 (m, 2H), 5.50 (s, 2H), 4.10 (m, 2H), 3.40 (d, J=10.97 Hz, 1H), 2.35 (m, 1H), 1.90–1.20 (m, 11H), 1.18 (t, J=7.13 Hz, 3H), 1.0 (m, 1H).

EXAMPLE XVIII

Methyl 2-cyclopentyl-2-[6-(quinolin-2-ylmethoxy)-naphth-2-yl]acetate

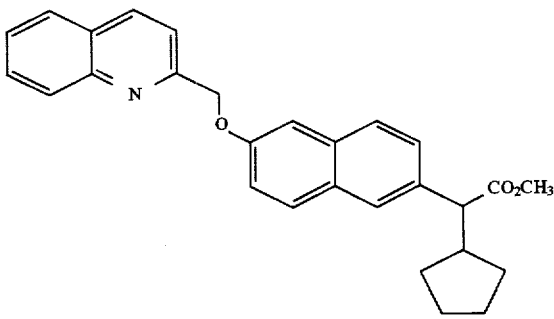

5.77 g (20.3 mmol) of the compound from Example VII and ground potassium carbonate (5.61 g, 40.6 mmol) are initially introduced into DMF (50.0 ml). The suspension is warmed to 50° C. for 1 hour. Solid 2-(chloromethyl)quinoline hydrochloride is carefully added to this suspension. It is stirred overnight at 50° C. The suspension is cooled and treated with about 50 ml of cold water. The resulting precipitate is filtered off with suction and dried:

Yield: 7.81 g (91%);

m.p.=124° C.

R$_f$=0.59 (50:1, CH$_2$Cl$_2$:methanol);

mass (calculated) for $C_{28}H_{27}NO_3=425.53$; mass spectrum (EI, rel. intensity) 425 (100%), 142 (80%);

$^1$H NMR (200 MHz, CDCl$_3$) δ8.17 (d, J=8.57 Hz, 1H), 8.10 (d, J=7.67 Hz, 1H), 7.90–7.50 (m, 6H), 7.43 (dd, J=8.52 Hz, J 1.74 Hz, 1H), 7.30–7.20 (m, 3H), 5.50 (s, 2H), 3.63 (s, 3H), 3.39 (d,J=11.12 Hz, 1H), 2.65 (m, 1H), 1.95 (m, 1H), 1.70–1.20 (m, 6H), 1.05 (m, 1H).

EXAMPLE XIX

Methyl 2-(5-(quinolin-2-ylmethoxy)-pyridin-2-yl)2-cycloheptylacetate

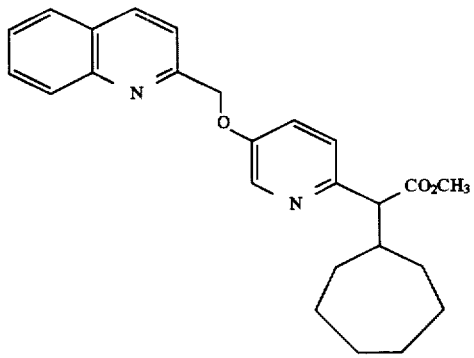

2-Chloromethylquinoline hydrochloride (6.07 g, 28.3 mmol), 7.0 g(28.3 mmol) of the compound from Example X and ground potassium carbonate (7.82 g, 56.6 mmol) are stirred overnight in DMF (100 ml) at 40° C. The mixture is cooled and 150 ml of water are added dropwise. The resulting precipitate is filtered off with suction and dried. The crystals are recrystallized from methanol and dried:

Yield: 7.44 g (65%);

m.p.=115° C.;

$R_f$=0.21 (3:1, petroleum ether:ethyl acetate);

mass (calculated) for $C_{25}H_{28}N_2O_3$=404.51; mass spectrum (FAB, rel. intensity) 405 (100%), 345 (20%), 308 (20%);

$^1$H NMR (250 MHz, CDCl$_3$/TMS) δ8.39 (m, 1H), 8.2 (d, J=8.51 Hz, 1H), 8.08 (d, J=8.36 Hz, 1H), 7.83 (dd, J=8.14 Hz, J=0.86 Hz, 1H), 7.74 (m, 1H), 7.65 (d,J=8.51 Hz, 1H), 7.30 (m, 1H), 7.33–7.25 (m, 2H), 5.39 (s, 2H), 3.64 (s, 3H), 3.60 (d, J=10.63 Hz, 1H), 2.38 (m, 1H), 1.85–1.25 (m, 11H), 1.08 (m, 1H).

EXAMPLE XX

Methyl 2-(5-(2-chlorobenzyloxy)-pyridin-2-yl)-2-cycloheptylacetate

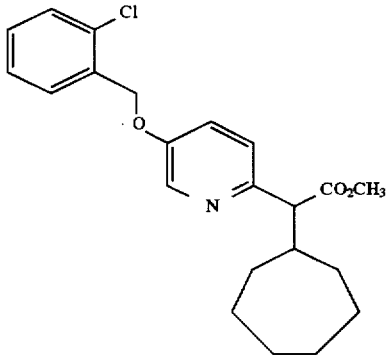

Sodium hydride (1.0 g, 4.87 mmol, 60% in paraffin) is initially introduced into DMF (1 ml) and cooled to 0° C. 1.09 g (4.42 mmol) of the compound from Example X are dissolved in DMF (9 ml) and added dropwise; the temperature rises to room temperature for 15 minutes, then the mixture is again cooled to 0° C. A solution of o-chlorobenzyl bromide, (1.0 g, 4.87 mmol), dissolved in DMF (1 ml), is then added dropwise. The mixture is allowed to warm to room temperature and, after 3 hours, water is added and it is extracted 3× with diethyl ether. The combined organic phases are dried over Na$_2$SO$_4$ and concentrated in a rotary evaporator. The residue is purified by column chromatography;

Yield: 1.43 g (83%)

$R_f$=0.59 (3:1; petroleum ether:ethyl acetate);

mass (calculated) for $C_{22}H_{26}ClNO_3$=387.91; mass spectrum (EI, rel. intensity) 387 (5%), 328 (15%), 291 (60%), 196 (40%), 181 (65%), 166 (100%);

$^1$H NMR (200 MHz, CDCl$_3$/TMS) δ8.33 (d, J=2.79 Hz, 1H), 7.53 (m, 1H), 7.41 (m, 1H), 7.34–7.20 (m, 4H), 5.18 (s, 2H), 3.65 (s, 3H), 3.59 (d, J=10.66 Hz 1H), 2.40 (m, 1H), 1.90–1.35 (m, 11H), 1.10 (m, 1H).

EXAMPLE XXI

Methyl 2-(5-(quinolin-2-ylmethoxy)-pyridin-2-yl)2-cylopentylacetate

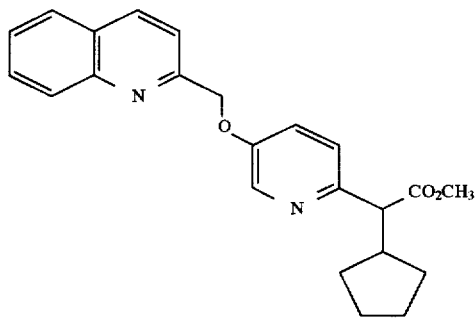

The reaction is carried out analogously to the procedure of Example XIX using 2-(chloromethyl)quinoline hydrochloride (0.264 g, 1.23 mmol), ground potassium carbonate (0.341 g, 2.46 mmol) and 0.290 g (1.23 mmol) of the compound from Example XI:

Yield: 0.365 g (79%);

m.p.=123° C.

$R_f$=0.14 (50:1, CH$_2$Cl$_2$:methanol);

$R_f$=0.46 (20:1, CH$_2$Cl$_2$:methanol);

mass (calculated) for $C_{23}H_{24}N_2O_3$=376.46; mass spectrum (FAB, rel. intensity) 377 (100%);

$^1$H NMR (250 MHz, CDCl$_3$/TMS) δ8.38 (m, 1H), 8.21 (d, J=8.50 Hz, 1H), 8.08 (d, J=8.43 Hz, 1H), 7.84 (dd, J=8.17 Hz, J=1.00 Hz, 1H), 7.75 (m, 1H), 7.65 (d, J=8.52 Hz, 1H), 7.56 (m, 1H), 7.27 (m, 2H), 5.39 (s, 2H), 3.65 (s, 3H), 3.54 (d, J=11.05 Hz, 1H), 2.65 (m, 1H), 1.92 (m, 1H), 1.70–1.20 (m, 6H), 1.10 (m, 1H).

EXAMPLE XXII

Ethyl 2-cycloheptyl-2-[5-(quinolin-2-ylmethoxy)-thiophen-2-yl]acetate

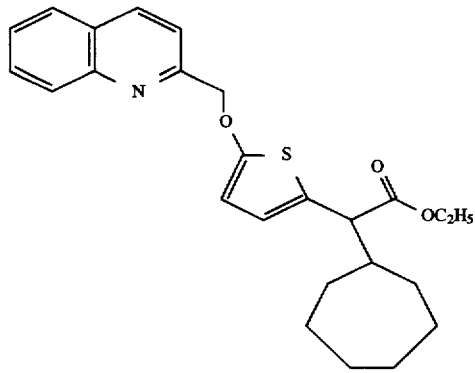

2-(Hydroxymethyl)quinoline (1.0 g 6.3 mmol) is dissolved in tert-butanol (10 ml) and sodium hydride (0.25 g 6.3 mmol) is slowly added to this solution. The mixture is stirred at 60° C. for 30 minutes and then heated to 100° C. 2.18 g (6.3 mmol) of the compound from Example XII and copper(I) bromide (0.09 g 0.63 mmol) are added and the mixture is stirred overnight at 100° C. As little reaction has taken place, further copper(I) bromide is added (0.81 g, 5.7 mmol). The mixture is again stirred at 100° C. for 3 hours and cooled, CH₂Cl₂ and saturated NH₄Cl solution are added and the mixture is extracted. The organic phase is dried over sodium sulphate and concentrated in a rotary evaporator. The residue is purified by column chromatography:

Yield: 0.10 g (2%)

$R_f$=0.25 (10:1; petroleum ether:ethyl acetate);

mass (calculated) for $C_{25}H_{29}NO_3S$=423.57; mass spectrum (FAB. rel. intensity) 424 (100%), 143 (90%).

EXAMPLE XXIII

N-(tert-Butoxycarbonyl)-4-(quinolin-2-ylmethoxy) piperidine

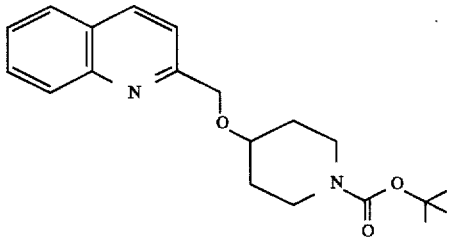

50.7 g (252 mmol) of the compound from Example XV are dissolved in DMF (500 ml) and cooled to 0° C. Sodium hydride (31.7 g, 792 mmol, 60% in paraffin) and triethylamine (20 drops) are added in portions to this solution. It is stirred at room temperature for 2 hours until evolution gas is no longer to be observed. 2-(chloromethyl)quinoline hydrochloride (77.2 g, 360 mmol) is slurried in DMF (1000 ml) and slowly added. The suspension is stirred overnight at room temperature. The mixture is poured onto water (3000 ml) and extracted 2× with diethyl ether. The combined organic phases are washed with water, then dried over Na₂SO₄ and concentrated in a rotary evaporator. The residue is purified by flash chromatography:

Yield: 90 g (>100%)

$R_f$=0.20 (3:1; petroleum ether:ethyl acetate);

mass (calculated) for $C_{20}H_{26}N_2O_3$=342.44; mass spectrum (FAB. rel. intensity) 342 (10%), 158 (100%), 143 (65%), 57 (100%);

¹H NMR (200 MHz, CDCl₃/TMS) δ8.18 (d, J=8.54 Hz, 1H), 8.04 (d, J=8.47 Hz, 1H), 7.82 (dd, J=8.17 Hz, J=1.1 Hz, 1H), 7.72 (m, 1H), 7.65 (d, J=8.53 Hz, 1H) 7.54 (m, 1H), 4.85 (s, 2H, O<u>CH</u>₂-quinoline), 3.86–3.71 (m, 2H, N<u>CH</u>₂CH₂), 3.65 (m, 1H, quinoline-CH₂O<u>CH</u>(CH₂—)₂), 3.17–3.04 (m, 2H, N<u>CH</u>₂CH₂), 1.97–1.85 (m, 2H), 1.72–1.55 (m, 2H), 1.46 (s, 9H, NCO₂C(CH₃)₃).

EXAMPLE XXIV

Methyl 2-phenyl-[4-(quinolin-2-ylmethoxy)-piperidin-1-yl]acetate

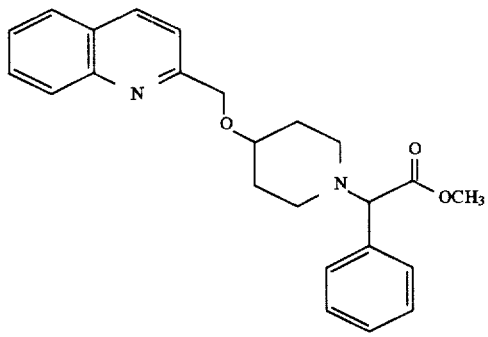

Sulphuric acid (20 ml) is carefully added dropwise to a solution, cooled to 0° C., of 4.8 g (13.4 mmol) of the compound from Example XVI and methanol (20 ml). The mixture is heated at reflux overnight. It is cooled and adjusted to pH=14 using conc. sodium hydroxide solution. The mixture is extracted with ethyl acetate and the combined organic phases are dried over Na₂SO₄ and concentrated in a rotary evaporator. The residue is purified by flash chromatography:

Yield: 2.3 g (44%)

$R_f$=0.30 (1:1; ethyl acetate):petroleum ether;

mass (calculated) for $C_{24}H_{26}N_2O_3$=390.48; mass spectrum (FAB. rel. intensity) 391 (100%), 232 (40%);

¹H NMR (250 MHz, CDCl₃/TMS) δ8.15(d, J=8.49 Hz, 1H), 8.02 (d, J=8.28 Hz, 1H), 7.81 (dd, J=8.10 Hz, J=1.0 Hz, 1H), 7.69 (m, 1H), 7.62 (d, J=8.57 Hz, 1H), 7.51 (m, 1H), 7.44–7.38 (m, 2H, Ph-<u>H</u>), 7.36–7.28 (m, 3H, Ph-<u>H</u>), 4.81 (s, 1H, O<u>CH</u>₂-quinoline), 4.03 (s, 1H, N<u>CH</u>(Ph)CO₂CH₃), 3.68 (s, 3H, CO₂<u>CH</u>₃), 3.52 (m, 1H, quinoline-CH₂O<u>CH</u>(CH₂—)₂), 2.80–2.68 (m, 2H, N<u>CH</u>₂CH₂), 2.31–2.13 (m, 2H, N<u>CH</u>₂CH₂), 2.05–1.89 (m, 2H), 1.83–1.70 (m, 2H).

EXAMPLE XXV

2-[(5-Quinolin-2-yl-methoxy)-pyridin-2-yl]-2-cyclopentyl acetic acid

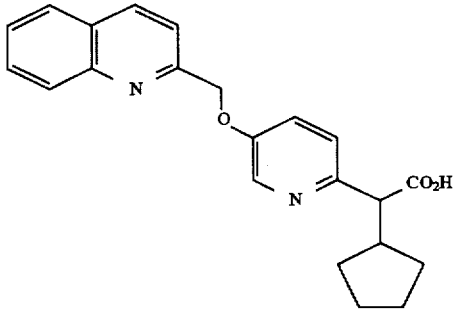

0.355 g (0.94 mmol) of the compound from Example XXI is heated at reflux overnight with 2N sodium hydroxide solution (1 ml) in methanol (10 ml). The solution is cooled and neutralized with 2N hydrochloric acid, and the solvent is stripped off in a rotary evaporator. The residue is dissolved in CH₂Cl₂ and the solution is washed with water. The organic phase is dried over sodium sulphate and concentrated in a rotary evaporator. The residue is purified by column chromatography (silica gel 60. Merck 40–63 μm. $CH_2Cl_2$:methanol. 100:10):

Yield: 0.250 g (73% of theory);
$R_f$=0.36 ($CH_2Cl_2$:methanol, 100:10)
M.p.=70° C. (foam)
MS (FAB+VE*HMR) 363 (100).

The compounds shown in Table I are prepared in analogy to the procedure of Example XXV:

solution is heated at reflux overnight. It is cooled and neutralized using 1N hydrochloric acid. The ethanol is stripped off in a rotary evaporator, the residue is taken up in water and $CH_2Cl_2$ and the solution is extracted. The combined organic phases are dried over $Na_2SO_4$ and concentrated in a rotary evaporator. The residue is purified by column chromatography and then employed further in not completely pure form:

Yield: 0.02 g (22%)

TABLE I $$A-H_2C-O-D\underset{R^1}{\overset{}{\diagdown}}CO_2H$$

| Ex. No. | A | D | $R^1$ | Yield (% of th.) | $R_f$ (solvent) | MS (FAB) | M.p. (°C.) | Starting material Ex. No. |
|---|---|---|---|---|---|---|---|---|
| XXVI | 2-Cl-phenyl | 2-pyridyl | (R&S) cHept | 90 | 0.34 (I) | 373 (80%) 231 (100%) | foam | XX |
| XXVII | quinolin-2-yl | 2-pyridyl | (R&S) cHept | 21 | 0.31 (I) | 391 (20%) 176 (100%) | >235 | XIX |
| XXVIII | quinolin-2-yl | 2-naphthyl | (R&S) cHept | 89 | 0.11 (H) 0.59 (J) | — | 112 | XVII |
| XXIX | quinolin-2-yl | 2-naphthyl | (R&S) cPent | 86 | 0.14 (I) | 412 (100%) 154 (555) | 234 | XVIII |

Preparation Examples

Example 1

2-Cycloheptyl-N-(2-hydroxy-1(R)-phenylethyl)-2-[5-(quinoline-2-ylmethoxy)thiophen-2-yl]acetamide

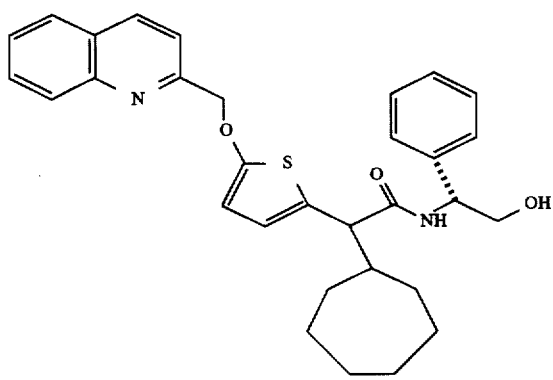

a)

1N sodium hydroxide solution (0.45 ml, 0.24 mmol) is added dropwise to a solution of 0.1 g (0.23 mmol) of the compound of Example XXII and ethanol (2.5 ml). The b)

A solution of R-phenylglycinol (7 mg, 0.05 mmol) and $CH_2Cl_2$ (2 ml) is initially introduced. 20 mg (0.05 mmol) of the compound mentioned under a) and 1-hydroxybenzotriazole (7.5 mg, 0.056 mmol) are added to this mixture. It is cooled to 10° C. and then treated with N'-(3-dimethylaminopropyl)-N'-ethylcarbodiimide (11 mg, 0.058 mmol) and triethylamine (10.2 mg, 0.101 mmol). The mixture is stirred overnight at room temperature. The solution is purified by column chromatography without working up:

Yield: 8.7 mg (33%);

$R_f$=0.46; ($CH_2Cl_2$:methanol, 20:1)

Mass (calculated) for $C_{31}H_{34}N_2O_3S$=514.69; mass spectrum (FAB, rel. intensity) 515 (100%), 350 (25%), 154 (80%), 143 (80%), 136 (65%);

Example 2

N-Benzyl-2-phenyl-2-[4-quinolin-2-ylmethoxy)-piperidin-1-yl]acetamide

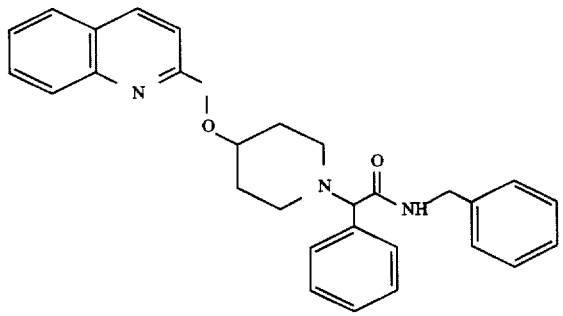

Trimethylaluminium (1.53 ml, 3.07 mmol, 2M in hexane) is initially introduced into toluene (10 ml) under argon. The mixture is cooled to 0° C., benzylamine (0.301 g, 2.82 mmol) is added dropwise and the mixture is stirred at room temperature for 1 hour. 1.0 g (2.56 mmol) of the compound from Example XXIV is dissolved in toluene (10 ml) and added dropwise. The mixture is stirred at 90° C. overnight. It is cooled, water is added and the mixture is stirred vigorously for 10 minutes. It is extracted 2× with ethyl acetate, and the combined organic phases are dried over $Na_2SO_4$ and concentrated in a rotary evaporator. The residue is purified by flash chromatography:

Yield: 0.5 g (42%)

$R_f$=0.13 (1:1; petroleum ether:EtOAc);

mass (calculated) for $C_{30}H_{31}N_3O_2$=465.60.

Mass spectrum (FAB, rel. intensity) 466 (100%), 331 (90%), 91 (65%);

$^1$H NMR (200 MHz, CDCl$_3$) δ8.15 (d, J=8.50 Hz, 1H), 8.02 (d, J=8.51 Hz, 1H), 7.81 (dd, J=8.11 Hz, J=1.16 Hz, 1H), 7.70 (m, 1H), 7.59 (d, J=8.49 Hz, 1H) 7.58–7.40 (m, 2H), 7.38–7.19 (m, 10H), 4.78 (s, 2H), 4.48 (d, J=5.98 Hz, 2H), 3.91 (s, 1H), 3.49 (m, 1H, quinoline-O$\underline{CH}$(CH$_2$—)$_2$), 2.85–2.60 (m, 2H, NC$_2$CH$_2$), 2.20 (m, 1H), 2.10–1.80 (m, 3H), 1.75–1.55 (m, 2H).

The compounds shown in Table 1 are prepared in analogy to the procedure of Example 1b:

TABLE 1

$$A-CH_2-O-D\underset{R^1}{\underset{|}{C}}\overset{O}{\overset{\|}{C}}-\underset{H}{\underset{|}{N}}-\overset{R^3}{\overset{|}{CH}}-R^4$$

| Ex. No. | A | D | R¹ | R³ |
|---|---|---|---|---|
| 3 | 2-Cl-phenyl | pyridyl | (R&S) cHept | (R)-phenyl |
| 4 | 2-Cl-phenyl | pyridyl | (R&S) cHept | phenyl |
| 5 | quinolinyl | pyridyl | (R&S) cPent | (R)-phenyl |
| 6 | quinolinyl | pyridyl | (R&S) cHept | (R)-phenyl |
| 7 | quinolinyl | naphthyl | (R&S) cHept | (R)-phenyl |
| 8 | quinolinyl | naphthyl | (R&S) cPent | (R)-phenyl |

TABLE 1-continued

| Ex. No. | (quinoline) | (aryl) | | R³ group |
|---|---|---|---|---|
| 9 | quinoline | naphthalene | (R&S) cPent | cyclohexyl |
| 10 | quinoline | naphthalene | (R&S) cPent | phenyl-OH, OCH₃ |
| 11 | quinoline | naphthalene | (R&S) cPent | -(S)-phenyl |
| 12 | quinoline | naphthalene | (R&S) cPent | p-tolyl (CH₃) |
| 13 | quinoline | pyridine | (S) cHept | (R)-phenyl |
| 14 | quinoline | pyridine | (R) cHept | (R)-phenyl |

| Ex. No. | $R^4$ | Yield (% of th.) | $R_f$ (solvent) | MS (FAB, rel. intens.) | M.p. (°C.) | Starting material Ex. No. |
|---|---|---|---|---|---|---|
| 3 | —CH₂OH | 83 | 0.40 (I) | 493 (100%), 328 (80%) | 122 | XXVI |
| 4 | H | 49 | 0.56 (H) | 463 (100%), 328 (60%) | 124 | XXVI |
| 5 | —CH₂OH | 74 | 0.28 (I) | 482 (100%), 317 (80%) | 110 | XXV |
| 6 | —CH₂OH | 72 | 0.18 (I) | 510 (100%), 345 (65%) | 58 | XXVII |
| 7 | —CH₂OH | 60 | 0.26 (H) | 559 (80%), 307 (100%) | — | XXVIII |
| 8 | —CH₂OH | 84 | 0.41 (I) | 531 (35%), 143 (100%) | 93 (foam) | XXIX |
| 9 | H | 72 | 0.70 (I) | 507 (45%), 143 (100%) | 184 (foam) | XXIX |
| 10 | H | 78 | 0.47 (I) | 547 (40%), 142 (90%), 137 (100%) | 108 (foam) | XXIX |
| 11 | —CH₂OH | 63 | 0.35 (I) | 531 (30%), 143 (100%) | 100 (foam) | XXIX |

TABLE 1-continued

| 12 | H | 83 | 0.77 (I) | 515 (20%), 105 (100%) | 95 (foam) | XXIX |
|----|---|----|----|----|----|----|
| 13 | CH$_2$OH | | 0.51 (I) | | 140 | 6 |
| 14 | CH$_2$OH | | 0.50 (I) | | 150 | 6 |

We claim:

1. Heterocyclic-substituted acetamide compounds of the formula (I):

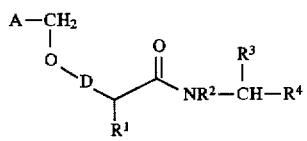

in which

A represents quinolyl or isoquinolyl, each of which is optionally substituted up to 3 times by identical or different substituents independently selected from the group consisting of halogen, nitro, cyano, trifluoromethyl, hydroxyl, carboxyl or straight-chain or branched alkyl, alkoxy, acyl or alkoxycarbonyl each having up to 8 carbon atoms, D represents naphthyl, cycloalkyl having 3 to 6 carbon atoms, pyridyl, furyl, thienyl or azetidinyl, each of which is optionally substituted up to 2 times by identical or different substituents independently selected from the group consisting of halogen, cyano, hydroxyl or straight-chain or branched alkyl or alkoxy each having up to 4 carbon atoms, R$^1$ represents hydrogen, cycloalkyl having 3 to 10 carbon atoms or straight-chain or branched alkyl having 1 to 10 carbon atoms, or represents phenyl which is optionally substituted up to 2 times by identical or different substituents independently selected from the group consisting of halogen, cyano, hydroxyl or straight-chain or branched alkyl or alkoxy each having up to 4 carbon atoms, R$^2$ represents hydrogen or straight-chain or branched alkyl having up to 3 carbon atoms, R$^3$ represents hydrogen, straight-chain or branched alkyl having up to 5 carbon atoms, benzyl, or cycloalkyl having 3 to 7 carbon atoms, or represents phenyl, pyridyl, furyl, or thienyl, each of which is optionally substituted up to 3 times by identical or different substituents independently selected from the group consisting of halogen, nitro, phenyl, hydroxyl or straight-chain or branched alkyl or alkoxy each having up to 6 carbon atoms, R$^4$ represents hydrogen or a group of the formula —CH$_2$OH or —CH$_2$—O—CO—R$^5$, in which R$^5$ represents hydrogen, straight-chain or branched alkyl having up to 8 carbon atoms or phenyl which is optionally substituted up to 3 times by identical or different substituents independently selected from the group consisting of halogen, hydroxyl, cyano or straight-chain or branched alkyl or alkoxy each having up to 4 carbon atoms, and salts thereof.

2. The compound according to claim 1 in which

A represents quinolyl, or isoquinolyl, each of which is optionally substituted identically or differently up to 2 times by fluorine, chlorine, bromine, nitro, cyano, trifluoromethyl, hydroxyl, carboxyl or straight-chain or branched alkyl, alkoxy, acyl or alkoxycarbonyl each having up to 6 carbon atoms, D represents naphthyl, cyclobutyl, cyclohexyl, pyridyl, furyl, thienyl, azetidinyl, each of which is optionally substituted by fluorine, chlorine, bromine, cyano, hydroxyl, methyl or methoxy, R$^1$ represents hydrogen, cyclobutyl, cyclopentyl, cyclohexyl, cycloheptyl, cyclooctyl or straight-chain or branched alkyl having up to 7 carbon atoms, or represents phenyl which is optionally substituted by fluorine, chlorine, bromine, cyano, hydroxyl or straight-chain or branched alkyl or alkoxy each having up to 3 carbon atoms, R$^2$ represents hydrogen or methyl, R$^3$ represents hydrogen or straight-chain or branched alkyl having up to 4 carbon atoms, benzyl, cyclopropyl, cyclopentyl, cyclohexyl or phenyl, pyridyl, thienyl or furyl, each of which is optionally substituted identically or differently up to 2 times by fluorine, chlorine, bromine, phenyl, nitro, hydroxyl or straight-chain or branched alkyl or alkoxy having up to 4 carbon atoms, and R$^4$ represents hydrogen or a group of the formula —CH$_2$—OH or —CH$_2$—O—CO—R$^5$, in which R$^5$ denotes hydrogen, straight-chain or branched alkyl having up to 6 carbon atoms or phenyl, which is optionally substituted identically or differently up to 2 times by fluorine, chlorine, bromine, cyano, hydroxyl or straight-chain or branched alkyl or alkoxy each having up to 3 carbon atoms, and their salts.

3. The compound according to claim 1 in which

A represents quinolyl, which is optionally substituted by fluorine, chlorine, bromine, cyano or straight-chain or branched alkyl, alkoxy, acyl or alkoxycarbonyl each having up to 3 carbon atoms, D represents naphthyl, cyclobutyl, cyclopentyl, cyclohexyl, furyl, pyridyl, thienyl, or azetidinyl, each of which is optionally substituted by fluorine, cyano, hydroxyl, methyl or methoxy, R$^1$ represents hydrogen, cyclohexyl, cycloheptyl, cyclooctyl or straight-chain or branched alkyl having up to 6 carbon atoms, or represents phenyl which is optionally substituted by fluorine, chlorine, cyano, hydroxyl, methyl, or methoxy, R² represents hydrogen or methyl, R³ represents hydrogen or straight-chain or branched alkyl having up to 3 carbon atoms, benzyl, cyclopropyl, cyclopentyl, cyclohexyl or pyridyl, thienyl or phenyl, each of which is optionally substituted identically or differently up to 2 times by fluorine, chlorine, bromine, nitro, phenyl, hydroxyl or straight-chain or branched alkyl or alkoxy having up to 3 carbon atoms, and R⁴ represents hydrogen, a group of the formula —CH₂—OH or —CH₂—O—CO—R⁵, in which R⁵ denotes straight-chain or branched alkyl having up to 6 carbon atoms or phenyl, which is optionally substituted identically or differently up to 2 times by fluorine, chlorine, bromine, cyano, hydroxyl, methyl or methoxy, and their salts.

4. The compound according to claim 1 wherein such compound is 2-cycloheptyl-N-(2-hydroxy-1(R)-phenylethyl)-2-[5-(quinoline-2-ylmethoxy)thiophen-2-yl]acetamido of the formula

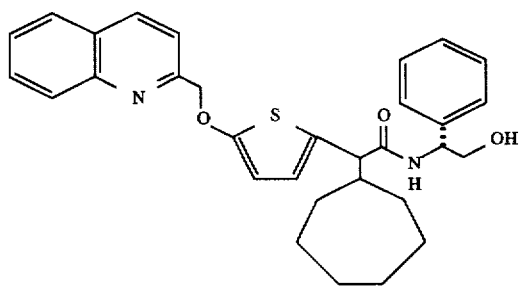

and salts thereof.

5. The compound according to claim 1 wherein such compound is 2-cyclopentyl-N-(2-hydroxy-1(R)-phenylethyl)-2-[5-quinoline-2-ylmethoxy)puridin-2-yl]acetamide of the formula

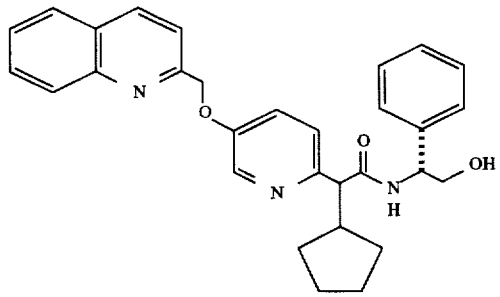

and salts thereof.

6. The compound according to claim 1 wherein such compound is 2-cyclopentyl-N-(2-hydroxy-1(R)-phenylethyl)-2-[6-(quinoline-2-ylmethoxy)naphth-2-yl]acetamide of the formula

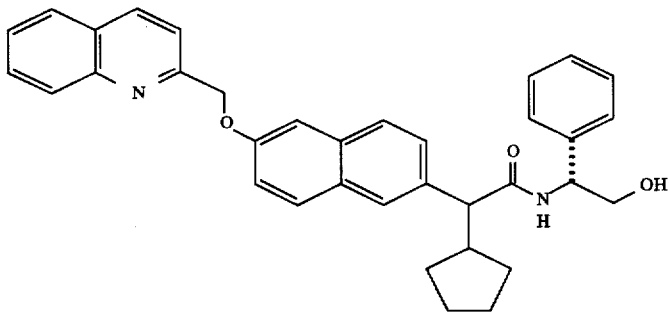

and salts thereof.

7. A composition for the treatment of atherosclerosis comprising an amount effective therefore of a compound or salt thereof according to claim 1 and a pharmacologically acceptable diluent.

8. The method of treating atherosclerosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO. : 5,747,505
DATED : May 5, 1998
INVENTOR(S) : Connell, et al.

It is certified that error appears in the above-indentified patent and that said Letters Patent is hereby corrected as shown below:

Col. 34, line 20    After " cyclobutyl " insert -- cyclopentyl --

Col. 34, line 21    After " thienyl, " insert -- or --

Signed and Sealed this

Eighth Day of December, 1998

Attest:

Attesting Officer

BRUCE LEHMAN

Commissioner of Patents and Trademarks